US00PP34014P2

(12) United States Plant Patent
Lim

(10) Patent No.: US PP34,014 P2
(45) Date of Patent: Mar. 15, 2022

(54) ***HIBISCUS* PLANT NAMED 'ALTMAMAMIYA'**

(50) Latin Name: *Hibiscus rosa-sinensis*
Varietal Denomination: ALTMAMAMIYA

(71) Applicant: Altman Specialty Plants, Inc, Vista, CA (US)

(72) Inventor: Peter Lim, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/356,879

(22) Filed: Jun. 24, 2021

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

*Primary Examiner* — June Hwu
(74) *Attorney, Agent, or Firm* — Cassandra Bright

(57) ABSTRACT

A new and distinct cultivar of *Hibiscus* plant named 'ALTMAMAMIYA' is disclosed, characterized by strongly ruffled, dark orange-red blooms with a darker base. Plants are dwarf and compact in habit, with dark, glossy foliage that is resistant to leaf spot disease. Flowering is continuous during the flowering season. The new variety is a *Hibiscus*, typically produced as an ornamental plant.

1 Drawing Sheet

Latin name of the genus and species: *Hibiscus rosa-sinensis.*

Variety denomination: 'ALTMAMAMIYA'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Jul. 15, 2015.

The seed parent is the unpatented *Hibiscus rosa-sinensis* 'City of New York'. The pollen parent is the variety *Hibiscus rosa-sinensis* 'Antigua Wind', U.S. Plant Pat. No. 23,656. The new variety was identified and selected as a potentially interesting selection in September of 2017. Selection was made at a commercial nursery in Vista, Calif.

Asexual reproduction of the new cultivar 'ALTMAMAMIYA' was first performed on September of 2017 in Vista, Calif., by vegetative cuttings. Subsequent propagation has shown that the unique features of this cultivar are stable and reproduced true to type in successive generations.

SUMMARY OF THE INVENTION

The cultivar 'ALTMAMAMIYA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTMAMAMIYA'. These characteristics in combination distinguish 'ALTMAMAMIYA' as a new and distinct *Hibiscus* cultivar:

1. Dark orange-red petals which are tightly overlapped and have a darker base, forming a dark eye.
2. Ruffled petals.
3. Dwarf compact bush constantly in bloom.

4. Dark dense glossy foliage which is highly disease resistant.

PARENT COMPARISONS

Plants of the new cultivar 'ALTMAMAMIYA' are similar to the seed parent, in most horticultural characteristics. However, characteristics of the new cultivar differ in the following:

1. Flowers of the new variety are orange-red, flowers of the seed parent are red.

Plants of the new cultivar 'ALTMAMAMIYA' are similar to the pollen parent, in most horticultural characteristics. However, characteristics of the new cultivar differ in the following:

1. Flowers of the new variety are orange-red, flowers of the pollen parent are rosy red.
2. Petals of the new variety are more ruffled than petals of the pollen parent.

COMMERCIAL COMPARISON

Plants of 'ALTMAMAMIYA' are similar in some horticultural characteristics to the variety *Hibiscus* 'Fire Wind', U.S. Plant Pat. No. 31,123. The new variety, however, differs in the following:

1. Flowers of 'ALTMAMAMIYA' are a different color red than flowers of 'Fire Wind'.
2. Plants of 'Fire Wind' have a taller growth habit than plants of 'ALTMAMAMIYA'.
3. Foliage of 'ALTMAMAMIYA' is darker green than foliage of 'Fire Wind'.

Plants of 'ALTMAMAMIYA' are similar in some horticultural characteristics to the variety *Hibiscus* 'Hot to Trot', unpatented. The new variety, however, differs in the following:

1. Flowers of 'ALTMAMAMIYA' are smaller than flowers of 'Hot to Trot'.

2. Plants of 'Hot to Trot' have a taller growth habit than plants of 'ALTMAMAMIYA'.
3. Flowers of 'ALTMAMAMIYA' have a darker eye not found on 'Hot to Trot'.

BRIEF DESCRIPTION OF THE PHOTOGRAPH

The accompanying photograph illustrates in full color a typical flower of 'ALTMAMAMIYA' from a plant grown outdoors at a commercial nursery in Vista, Calif. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'ALTMAMAMIYA' plant. This plant was grown at a commercial nursery in Vista, Calif. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTMAMAMIYA'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 2 years old.

Growth habit: Upright and compact.

Height: 48 cm.

Plant spread: 44 cm.

Branching characteristics: 2 to 4 breaks from a pinch, occurring at acute angles.

Length of primary lateral branches: 12 to 32 cm.

Quantity of lateral branches: About 10 to 14.

Characteristics of primary lateral branches:

- *Diameter.*—Average range 11 mm to 12 mm.
- *Color.*—New growth near RHS Green 143C, mature growth near RHS Greyed-Green 197B, striated Grey-Brown N199A.
- *Texture.*—New growth very slightly hirsute, older growth striated.

Internode length: 1.3 to 2.3 cm.

FOLIAGE

Leaf:

- *Arrangement.*—Alternate.
- *Quantity.*—Approximately 20 per branch.
- *Average length.*—9.5 cm, excluding petiole.
- *Average width.*—8 cm.
- *Shape of blade.*—Heart-shaped.
- *Apex.*—Acute.
- *Base.*—Cordate.
- *Margin.*—Crenate.
- *Texture of top surface.*—Glabrous.
- *Texture of bottom surface.*—Glabrous.
- *Color.*—Young foliage upper side: RHS Green 137A. Young foliage under side: RHS Green 137C. Mature foliage upper side: RHS Green 137A. Mature foliage under side: RHS Green 137B.
- *Venation.*—Type: Pinnate. Venation color, upper side: RHS Green 143C. Venation color, under side: RHS Green 143C.
- *Petiole.*—Length: 2.5 cm. Diameter: 3 to 4 mm. Color: RHS Green 137B, base and upper surface flushed Greyed- Purple 187A. Texture: Upper surface very slightly pubescent, lower surface glabrous.
- *Leaf stipule.*—Not observed present.

FLOWER

Natural flowering season: Late Spring through Summer.

Flower type and habit: Solitary, rotate.

- *Single, double, multiplex.*—Single.
- *Petals overlapping.*—Strongly overlapping.

Rate of flower opening: 1 to 2 days from bud to fully opened flower.

Flower longevity on plant: 1 to 2 days.

Persistent or self-cleaning: Self-cleaning.

Bud:

- *Shape.*—Ovate.
- *Length.*—3.5 cm.
- *Diameter.*—1.8 cm.
- *Color.*—RHS Green 143C, flushed Orange-Red N34B.

Flower size:

- *Diameter.*—12 cm.
- *Depth.*—8.5 cm.

Petals:

- *Quantity.*—5.
- *Arrangement.*—Whorled, strongly overlapping.
- *Length.*—8 cm.
- *Width.*—7.5 cm.
- *Shape.*—Broad spatulate.
- *Apex.*—Obtuse rounded with strong ruffles and shallow crenations.
- *Base.*—Attenuate.
- *Margin.*—Irregular, shallow crenations, strong ruffling.
- *Texture, upper and lower surfaces.*—Smooth, rugose on lower half.
- *Color.*—When opening, upper surface: Near RHS Red 42A, basal blotch (forming flower eye) near Orange-Red N34A. When opening, lower surface: RHS Orange-Red 34A, basal blotch faintly flushed near Orange-Red N34A. Fully opened, upper surface: Near RHS Red 42A, basal blotch (forming flower eye) near Orange-Red N34A. Fully opened, lower surface: RHS Orange-Red 34A, basal blotch faintly flushed near Orange-Red N34A. Ratio of basal blotch/eye to petal size: About 10% to 20% of petal blade blotched.

Sepals:

- *Quantity.*—5.
- *Length.*—2.8 cm.
- *Width.*—1.8 cm.
- *Shape.*—Narrow ovate.
- *Margin.*—Entire.

*Apex*.—Acute.
*Base*.—Fused.
*Color*.—Upper surface: RHS Yellow-Green 144A. Lower surface: RHS Yellow-Green 144A.
*Texture*.—Lower surface very short hirsute, upper surface glabrous.

Epicalyx:
*Quantity of bracts*.—5.
*Bract length*.—1.5 cm cm.
*Bract width*.—5 mm.
*Bract shape*.—Narrow deltate.
*Bract margin*.—Entire.
*Color*.—RHS Green 137A upper surface, Green 137B lower surface.
*Texture*.—Glabrous all surfaces.

Peduncles:
*Length*.—3.5 cm to 4.2 cm.
*Diameter*.—4 mm.
*Angle*.—Approximately 15° to the lateral branch.
*Strength*.—Strong.
*Texture*.—Roughly pubescent.
*Color*.—RHS Green 137B.

Fragrance: None.

REPRODUCTIVE ORGANS

Stamens:
*Number*.—About 50.
*Filament length*.—4 to 6 mm.
*Filament color*.—Near RHS Orange-Red 34B.

Anthers:
*Shape*.—Irregular sphere.
*Length*.—About 2 mm.
*Color*.—Near RHS Yellow-Orange 21A.
*Pollen color*.—Near RHS Yellow-Orange 21A.
*Pollen amount*.—Moderate.

Pistil:
*Number*.—1.
*Length*.—7 cm.
*Style*.—Length: 6.8 cm. Color: Lower section near RHS Orange-Red N34A, upper section near N34B.
*Stigma*.—Shape: Peltate. Color: Near RHS Orange-Red Red 34A.
*Ovary color*.—Near RHS Yellow-Green 145C.

OTHER CHARACTERISTICS

Seeds: Not observed.

Disease/pest resistance: Observed resistance to leaf spot disease (assumed *Pseudomonas syringae*). No other resistance nor susceptibility to normal diseases and pests of *Hibiscus rosa-sinensis* have been observed.

Temperature tolerance: USDA Zones 8 through 11.

What is claimed is:

1. A new and distinct cultivar of *Hibiscus* plant named 'ALTMAMAMIYA' as herein illustrated and described.

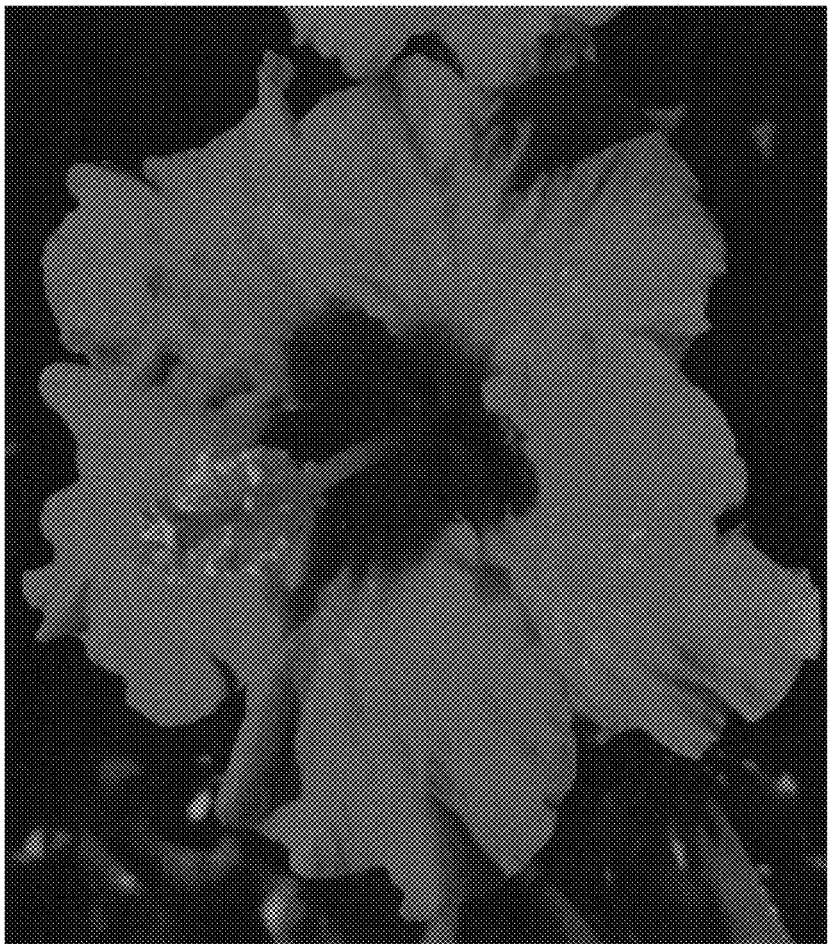

* * * * *